United States Patent

Karrer

[11] 3,946,084
[45] Mar. 23, 1976

[54] PHENOXYPHENYL 1-ALKOXY-3-METHYLBUTENYL ETHERS

[75] Inventor: Friedrich Karrer, Basel, Switzerland

[73] Assignee: Ciba-Geigy Corporation, Ardsley, N.Y.

[22] Filed: Aug. 23, 1974

[21] Appl. No.: 499,816

[30] Foreign Application Priority Data
Aug. 31, 1973  Switzerland.................... 12534/73
July 24, 1974  Switzerland.................... 10208/74

[52] U.S. Cl............................ 260/613 R; 424/341
[51] Int. Cl.²..................................... C07C 43/20
[58] Field of Search................. 260/613 R; 424/341

[56] References Cited
OTHER PUBLICATIONS
Chemical Abstracts, Vol. 77 (1972) p. 34, 136d.

*Primary Examiner*—V. D. Turner
*Attorney, Agent, or Firm*—Frederick H. Rabin

[57] ABSTRACT

Compounds of the formula

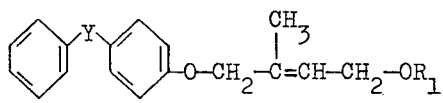

wherein
$R_1$ is $C_1$–$C_5$-alkyl, $C_3$–$C_5$-alkenyl or $C_3$-alkynyl and
Y represents an oxygen atom or the group —$CH_2$— and their use for the control of insects are disclosed.

5 Claims, No Drawings

PHENOXYPHENYL 1-ALKOXY-3-METHYLBUTENYL ETHERS

The present invention provides compounds of the formula

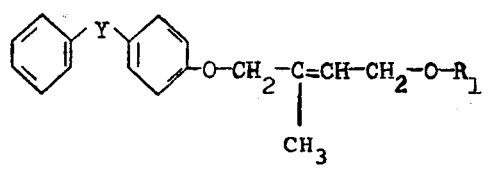   (I)

wherein $R_1$ represents alkyl with 1 to 5 carbon atoms, alkenyl with 3 to 5 carbon atoms or alkinyl with 3 carbon atoms, and Y represents oxygen or —$CH_2$—, a process for their manufacture and a method of using them in pest control.

The alkyl, alkenyl or alkinyl groups represented by $R_1$ can be straight-chain or branched. Examples of such groups include: methyl, ethyl, isopropyl, n-propyl, n-butyl, isobutyl, sec. butyl, tert.butyl, n-pentyl and isomers thereof, allyl, methallyl, propargyl.

Preferred compounds on account of their action are those of the formula I wherein $R_1$ represents methyl, ethyl, allyl or propargyl and Y represents oxygen or —$Ch_2$—.

The compounds of the formula I can be manufactured by methods which are known per se, e.g. according to the following reaction schemes:

I)

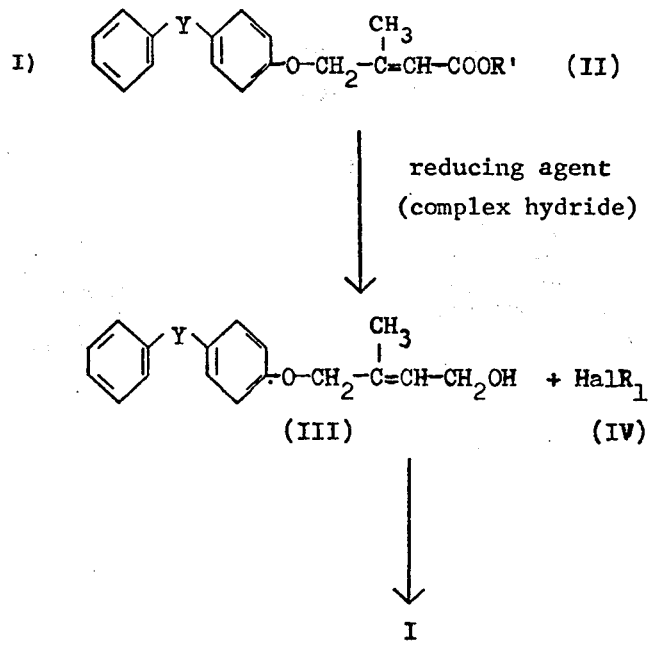

In the formulae II, III and IV, the symbols $R_1$ and Y have the meanings assigned to them in respect of the formula I and Hal represents a halogen atom, in particular chlorine, bromine or iodine and R' represents lower alkyl.

II)

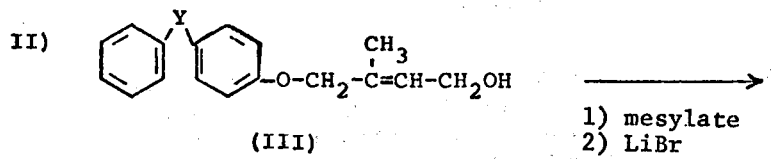

1) mesylate
2) LiBr

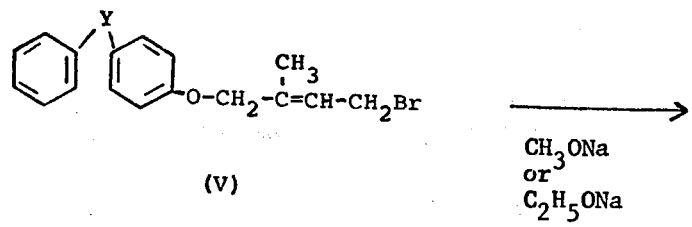

$CH_3ONa$
or
$C_2H_5ONa$

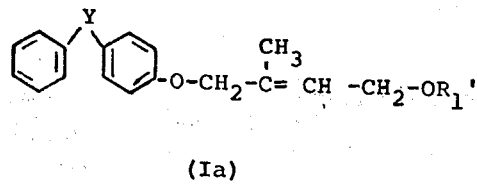

(Ia)

In the formulae III, V and Ia, Y has the meaning assigned to it in respect of the formula I and $R_1'$ represents methyl or ethyl.

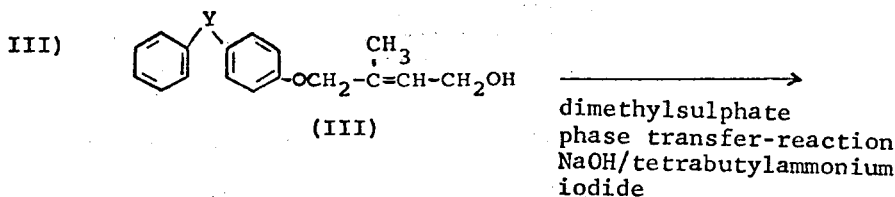

(III)

→ dimethylsulphate
phase transfer-reaction
NaOH/tetrabutylammonium iodide

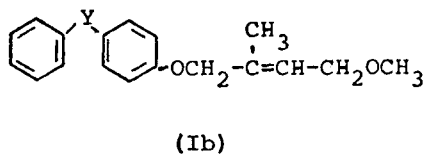

(Ib)

In the formulae III and Ib, Y has the meaning assigned to it in respect of the formula I.

The phase transfer catalysed ether formation from an alcohol and a dialkyl sulphate is described e.g. in Angew. Chemie/85, 868–869 (1973).

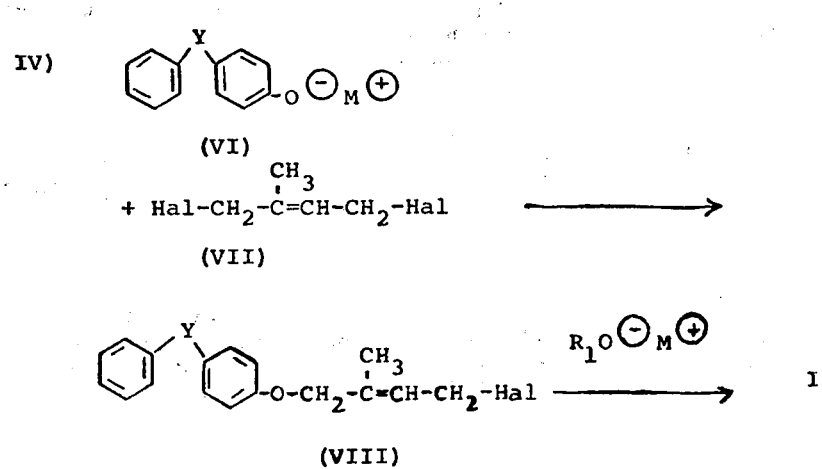

In the formulae VI, VII and VIII, Y has the meaning assigned to it in respect of the formula I, Hal is a halogen atom, in particular a chlorine or a bromine atom, and M is a metal, preferably sodium or potassium.

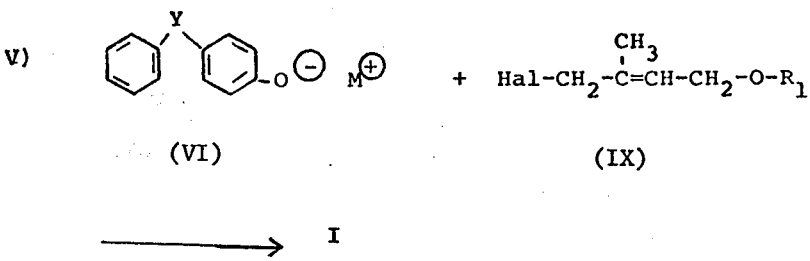

→ I

In the formulae VI and IX, the symbols Y and $R_1$ have the meanings assigned to them in respect of the formula I, Hal is a halogen atom, in particular a chlorine or a bromine atom, and M is a metal, preferably sodium or potassium.

The starting materials of the formulae II, VI, VII and IX are known or they can be manufactured by methods analogous to known ones. In the manufacture of the compounds of the formula I by the processes indicated hereinbefore, both possible geometrical isomers are formed in varying ratios. It is possible to obtain pure trans- or cis-isomers of the formula I e.g. by using pure cis- or trans-compounds of the formula II or by fractional crystallisation, fractionation, separation of cis-/trans-isomeric mixtures by chromatographic adsorption analysis or by gas chromatography.

Solvents used for the reduction of a 4-aryloxy-3-alkyl-2-butenoic acid ester (II) with the aid of a complex hydride, e.g. lithium aluminium hydride or sodium-dihydrido-bis(2-methoxyethoxy)-aluminate, are, for example, anhydrous ethers, such as diethyl ether, 1,2-dimethoxyethane, tetrahydrofuran, dioxan, anisol or hydrocarbons, e.g. benzene, toluene, xylene. The temperatures for this reduction are from −10° C to +70° C, but are normally between 0° C and 30° C.

Sodium-dihydrido-bis-(2-methoxyethoxy)-aluminate has the particular advantage that a surplus of it can also be used, which does not result in any partial reduction of the double bond in the side-chain.

The unsaturated alcohols of the formula III are isolated in the usual way by decomposition of the complex alcoholate formed as intermediate with water or a solvent that contains water and by extraction of the alcohol III. If necesary, an additional purification can be effected by high vacuum distillation or chromatographic adsorption analysis.

The complex alcoholate that is formed during the reduction of an ester II with complex hydrides can also be converted with alkyl halides into the desired ethers I direct, i.e. without intermediate isolation of the alcohol III, after addition of anhydrous, polar solvents, for example dimethyl formamide or hexamethylphosphoric triamide.

The compounds of the formula I can be used as cis/-trans mixtures or in the form of pure cis- or trans-compounds. The compounds of the formula I are suitable for combating insects of the families:

Tettigonidae, Gryllidae, Gryllotalpidae, Blattidae, Reduviidae, Phyrrhocoridae, Cimicidae, Delphacidae, Aphididae, Diaspididae, Pseudococcidae, Scarabaeidae, Dermestidae, Coccinellidae, Tenebrionidae, Chrysomelidae, Bruchidae, Tineidae, Noctuidae, Lymatriidae, Pyralidae, Culcidae, Tipulidae, Stomoxydae, Trypetidae, Muscidae, Calliphoridae and Pulicidae.

The insecticial action can be substantially broadened by addition of other insecticides and insect lures and adapted to given circumstances.

Examples of suitable additives are:
organic phosphorus compounds
derivatives of nitrophenols
formamidines
ureas
carbamates and
chlorinated hydrocarbons.

The etherification of alcohols of the formula III can also be effected in a manner which is known per se with alkylating reagents, e.g. alkyl, alkenyl or alkinyl halides, dialkyl sulphates, trialkyloxonium tetrafluorobroates (cf. for example H. Meerwein in Houben-Weyl, vol. VI/3, pp. 10–40). Preferably the alcohol of the formula III is converted into its alcoholate before the alkylation with alkyl, alkenyl or alkinyl halides, for example with alkali oxides or alkali hydrides.

Examples of inert solvents that can be used for the etherification with alkyl, alkenyl and alkinyl halides according to equation I are ethers, such as diethyl ether, tetrahydrofuran, dioxan, 1,2-dimethoxyethane etc., also hydrocarbons, dimethyl formamide or hexamethylphosphoric triamide.

The etherification according to equations IV or V can be carried out in inert solvents e.g. dioxan, tetrahydrofuran, 1,2-dimethoxyethane, dimethyl formamide or hexamethylphosphoric triamide, diethyl ether or hydrocarbons.

The reaction temperatures are between −10° C and +100° C, and are normally between 0° C and 70° C.

The alkylation with trialkyloxonium trialkyloxonium is carried out preferably between −10° C and +40° C in halogenated or non-halogenated hydrocarbons, e.g., in dichloromethane.

The compounds of the formula I may be used as pure active substance or together with suitable carriers and-/or additives. suitable carriers and additives can be solid or liquid and correspond to the substances conventionally used in formulation technique, for example natural or regenerated substances, solvents, dispersants, wetting agents, adhesives, thickeners, binders and/or fertilisers.

For application, the compounds of the formula I may be processed to dusts, emulsion concentrates granules, dispersions sprays, to solutions, or suspensions, in the conventional formulation which is commonly employed in application technology.

The agents according to the invention are manufactured in known manner by intimately mixing and/or grinding active substances of the formula I with the suitable carriers, optionally with the addition of dispersants or solvents which are inert towards the active substances. The active substances may take, and be used in, the following forms:

Solid forms:
Dusts, tracking agents, granules, coated granules, impregnated granules and homogeneous granules.

Liquid forms:
a. active substances which are dispersible in water: wettable powders, pasts, emulsions;
b. solutions.

The content of active substance in the above described agents is between 0 and 95%.

The active substances of the formula I can, for example, be formulated as follows:

Dusts
The following substances are used to manufacture (a) a 5% and (b) a 2% dust:

(a)

5 parts of active substance
95 parts of talcum (b)

2 parts of active substance
1 part of highly disperse silicic acid
97 parts of talcum.

The active subtances are mixed with the carriers and ground.

Granules
The following substances are used to produce 5% granules:
5 parts of active substance,
0.25 parts of epichlorohydrin,
0.25 parts of cetyl polyglycol ether,
3.50 parts of polyethylene glycol,
91 parts of kaolin (particle size 0.3 – 0.8 mm).

The active substance is mixed with epichlorohydrin and dissolved with 6 parts of acetone; the polyethylene glycol and cetyl polyglycol ether are then added. The thus obtained solution is sprayed on kaolin, and the acetone subsequently evaporated in vacuo.

Wettable powder:

The following constituents are used for the preparation of (a) a 40% (b) and (c) a 25%, and (d) a 10% wettable powder:

(a)

40 parts of active substance,
5 parts of sodium lignin sulphonate,
1 part of sodium dibutyl-naphthalene sulphonate,
54 parts of silicic acid.

(b)

25 parts of active substance,
4.5 parts of calcium lignin sulphonate,
1.9 parts of Champagne chalk/hydroxyethyl cellulose mixture (1:1),
1.5 parts of sodium dibutyl naphthalene sulphonate,
The 19.5 parts of silicic acid,
19.5 parts od Champagne chalk,
28.1 parts of kaolin.

(c)

25 parts of active substance,
2.5 parts of isooctylphenoxy-polyoxyethylene-ethanol,
1.7 parts of Champagne chalk/hydroxyethyl cellulose mixture (1:1),
8.3 parts of sodium aluminium silicate,
16.5 parts of kieselguhr,
46 parts of kaolin.

(d)

10 parts of active substance,
3 parts of a mixture of the sodium salts of saturated fatty alcohol sulphates,
5 parts of naphthalenesulphonic acid/formaldehyde condensate,
82 parts of kaolin.

The active substances are intimately mixed, in suitable mixers, with the additives, the mixture being then ground in the appropriate mills and rollers. Wettable powders are obtained which can be diluted with water to give suspensions of any desired concentration.
Emulsifiable concentrates:

The following substances are used to produce (a) a 10% and (b) a 25% emulsifiable concentrate:

(a)

10 parts of active substance,
34 parts of epoxidised vegetable oil,
13.4 parts of a combination emulsifier consisting of fatty alcohol polyglycol ether and alkylarylsulphonate calcium salt,
40 parts of dimethylformamide,
43.2 parts of xylene.
25 parts of active substance,
2.5 parts of epoxidised vegetable oil,
10 parts of an alkylarylsulphonate/fatty alcoholpolyglycol ether mixture,
5 parts of dimethylformamide,
57.5 parts of xylene.

From these concentrates it is possible to produce, by dilution with water, emulsions of any desired concentration.
Spray:

The following constituents are used to prepare a 5% spray:
5 parts of active substance,
1 part of epichlorohydrin,
94 parts of benzine (boiling limits 160° C – 190° C).

EXAMPLE 1

A 60% suspension of 2.42 g of sodium hydride in mineral oil is washed repeatedly with hexane while passing in nitrogen and subsequently covered with a layer of 50 ml of anhydrous tetrahydrofuran. With stirring, a solution of 15 g of 4-(p-phenoxy)-phenoxy-3-methyl-2-cis/trans-buten-1-ol in 30 ml of hexamethylphosphoric triamide is added dropwise to this suspension at room temperature over the course of half an hour and stirring is subsequently continued for 14 hours at room temperature and for 4 hours at 70° C. Upon formation of the sodium alcoholate, 13 g of ethyl iodide are added dropwise at 65°–70° C over the course of half an hour and stirring is continued for 3 hours at this temperature. The reaction mixture is processed by pouring it on 500 ml of ice water and repeatedly extracting it with water. The combined ethereal phases are washed with water and saturated sodium chloride solution and dried over sodium sulphate. The solvent is distilled off and the residue is then purified further by chromatography over silica gel (eluant: ether/hexane 1:5) to yield pure 1-ethoxy-3-methyl-4-(p-phenoxy)-phenoxy-2-cis/trans-butene; $n_D^{20} = 1.5521$. The 4-(p-phenoxy)-phenoxy-3-methyl-2-cis/transbuten-1-ol used as starting material is manufactured as follows:

With stirring, 70 ml of a 70% solution of sodium dihydridobis-(2-methoxyethoxy)-aluminate in benzene are added at 10° C over the course of one hour to a solution of 62.5 g of 4-(p-phenoxy)-phenoxy-3-methyl-2-butenoic acid ethyl ester in 350 ml of anhydrous benzene. After the mixture has been stirred for a further 4 hours at 15°–20° C, the complex alcoholate* that has formed is poured carefully on 1 litre of ice water. The aqueous phase is saturated with sodium chloride, the organic phase is isolated and the aqueous phase is extracted repeatedly with ether. The combined organic phases are dried over sodium sulphate, the solvent is distilled off completely and the 4-(p-phenoxy)-phenoxy-3-methyl-2-cis/trans-buten-1-ol is purified by chromatography over silica gel (eluant: ethyl acetate/-hexane 1:3); $n_D^{20} = 1.5781$.

*The aluminium alcoholate complex can also be converted into the 1-ethoxy-3-methyl-4-(p-phenoxy)-phenoxy-2-cis/trans-butene direct (i.e. without isolation of the alcohol) after addition of hexamethylphosphoric triamide with ethyl iodide at about 55° C. Processing and purification as described hereinabove.

the following intermediate of the formula III

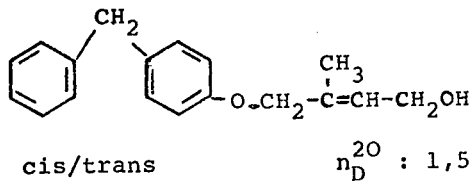

cis/trans      $n_D^{20} : 1,5770$ and the following end products of the formula I are manufactured in a manner analogous to that described hereinbefore:

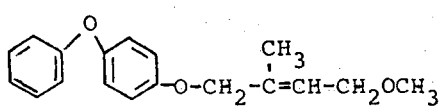

cis/trans      $n_D^{20}$ : 1,5571

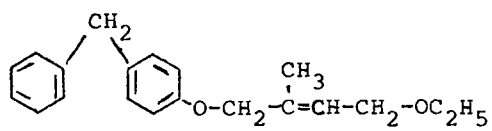

cis/trans      $n_D^{20}$ : 1,5500

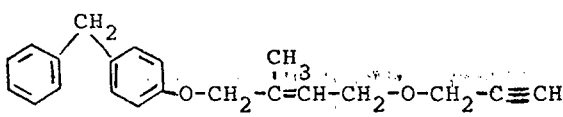

cis/trans      $n_D^{20}$ : 1,5738

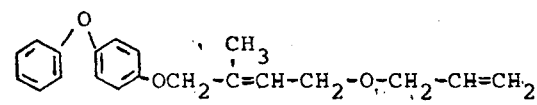

$n_D^{20}$ : 1,5682

EXAMPLE 2

Contact action on Dysdercus fasciatus larvae

A specific amount of a 0.1% active substance solution in acetone (corresponding to 10 mg of active substance per m²) was pipetted into an aluminium dish and uniformly distributed. After the acetone had evaporated, 10 Dysdercus fasciatus larvae in the 5th stage were put into the treated dish which contained feed and moist cotton wool. The dish was then covered with a screen top.

After about 10 days, i.e. as soon as the controls had moulted and emerged to the adult stage, the treated test subjects were examined for the number of adults.

The compounds according to Example 1 exhibited good action in the above test.

EXAMPLE 3

Contact action on Aedes aegypti larvae

About 20 two-day old larvae of the yellow fever fly (Aedes aegypti) are put into a beaker containing a solution of active substance (concentration 5 ppm).

The beaker was then covered with a screen top. After the control insects had finished moulting to emerge as adults, the test subjects were examined and the percentage number of normal adults was determined in comparison with the control. The compounds according to Example 1 exhibited good activity in the above test.

EXAMPLE 4

Contact action on Tenebrio molitor pupae

A specific amount of a 0.1% solution of active substance in acetone (corresponding to 10 mg of active substance/m²) was pipetted into an aluminium dish and evenly distributed. After the acetone had evaporated, 10 freshly shed pupae were placed on the treated surface. The dish was covered with a screen top.

After the controls had emerged from the cocoon as Imagines, the test subjects were examined for the number of normal adults.

The compounds according to Example 1 exhibited good activity in the above test.

EXAMPLE 5

Action against Ephestia kuhniella 50 g of wheat flour were mixed in two beakers with a specific amount of active substance formulated as 5% dust to give a concentration of 0.05%. Then 10 larvae of Ephestia kuhniella were put into each beaker (25 g of flour). Over the course of 8 weeks the development of the population was determined and the number of wings was ascertained.

Compounds according to Example 1 exhibited good activity in the above test.

I claim:

1. A compound of the formula

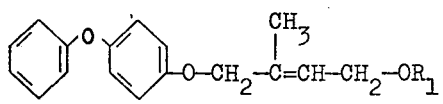

wherein
R$_1$ is C$_1$–C$_5$-alkyl, C$_3$–C$_5$-alkenyl or C$_3$-alkynyl.

2. A compound according to claim 1 wheren R$_1$ is methyl, ethyl, allyl or propargyl.

3. 1-Ethoxy-3-methyl-4-(p-phenoxy)-phenoxy-2-cis/-transbutene according to claim 2.

4. 1-Methoxy-3-methyl-4-(p-phenoxy)-phenoxy-2-cis/transbutene according to claim 2.

5. 1-Allyloxy-3-methyl-4-(p-phenoxy)-phenoxy-2-cis/transbutene according to claim 2.

* * * * *